US012727781B2

(12) United States Patent
Nair et al.

(10) Patent No.: US 12,727,781 B2
(45) Date of Patent: Sep. 8, 2026

(54) SYSTEMS AND METHODS FOR LUNG COMPLIANCE IMAGING

(71) Applicant: William Beaumont Hospital, Royal Oak, MI (US)

(72) Inventors: Girish B. Nair, Royal Oak, MI (US); Edward Castillo, Houston, TX (US)

(73) Assignee: WILLIAM BEAUMONT HOSPITAL, Royal Oak, MI (US)

( * ) Notice: Subject to any disclaimer, the term of this patent is extended or adjusted under 35 U.S.C. 154(b) by 369 days.

(21) Appl. No.: 18/438,718

(22) Filed: Feb. 12, 2024

(65) Prior Publication Data

US 2024/0260851 A1 Aug. 8, 2024

Related U.S. Application Data

(63) Continuation of application No. 17/314,317, filed on May 7, 2021, now Pat. No. 11,931,143.

(Continued)

(51) Int. Cl.
*A61B 5/085* (2006.01)
*A61B 5/091* (2006.01)

(Continued)

(52) U.S. Cl.
CPC .............. *A61B 5/085* (2013.01); *A61B 5/091* (2013.01); *A61B 6/032* (2013.01); *G06T 7/62* (2017.01);

(Continued)

(58) Field of Classification Search
CPC ......... A61B 5/085; A61B 5/091; A61B 6/032; A61B 5/055; A61B 5/08; A61B 5/113; A61B 6/463; A61B 6/5217; A61B 2576/02; G06T 7/62; G06T 2207/10076; G06T 2207/10081; G06T 2207/10088; G06T 2207/20048; G06T 2207/30061; G06T 7/254; G06T 7/0016
See application file for complete search history.

(56) References Cited

U.S. PATENT DOCUMENTS

2016/0180528 A1 6/2016 Reynolds
2016/0292864 A1 10/2016 Dabbah
2020/0330795 A1 10/2020 Sawant

OTHER PUBLICATIONS

"Magnetic resonance imaging for quantitative assessment of lung aeration: a pilot translational study." Frontiers in Physiology 9 (2018): 1120.) (Year: 2018).*

(Continued)

*Primary Examiner* — Wassim Mahrouka
(74) *Attorney, Agent, or Firm* — Honigman LLP; Thomas J. Appledorn

(57) ABSTRACT

A method for computing lung compliance imaging, the method comprising obtaining one or more images of lungs, determining a spatial transformation of each voxel within the lungs between the lungs at an inhale position and the lungs at an exhale position to provide displacement vector estimates for each voxel within the lungs, performing volume change inference operations to determine a volume change between the lungs at the inhale position and the lungs at the exhale position based on an inhale region of interest, an exhale region of interest, and the displacement vector estimates for each voxel within the lungs, computing a lung compliance based on the volume change inference operations.

20 Claims, 5 Drawing Sheets

Low Compliance  High Compliance

Related U.S. Application Data

(60) Provisional application No. 63/021,754, filed on May 8, 2020.

(51) Int. Cl.
*A61B 6/03* (2006.01)
*G06T 7/62* (2017.01)

(52) U.S. Cl.
CPC .............. *G06T 2207/10076* (2013.01); *G06T 2207/10081* (2013.01); *G06T 2207/10088* (2013.01); *G06T 2207/20048* (2013.01); *G06T 2207/30061* (2013.01)

(56) References Cited

OTHER PUBLICATIONS

Compliance measurements of the upper airway in pediatric Down syndrome sleep apnea patients. Annals of biomedical engineering 44, No. 4 (2016): 873-885 (Year: 2016).*
Registration-based estimates of local lung tissue expansion compared to xenon CT measures of specific ventilation. Medical image analysis 12, No. 6 (2008): 752-763 (Year: 2008).*
Albert, MS, et al. Biological magnetic resonance imaging using laser-polarized 129Xe. Nature. 1994;370:199. PubMed PMID: 8028666.
Altes, TA, et al. Hyperpolarized helium-3 magnetic resonance lung imaging of non-sedated infants and young children: a proof-of-concept study. Clin Imaging. 2017;45:105-10.
Bárány, I., et al. Computing the volume is difficult. Discrete & Computational Geometry. 1987;2(4):319-326.
Bauman, G, et al. Non-contrast-enhanced perfusion and ventilation assessment of the human lung by means of fourier decomposition in proton MRI. Magn Reson Med. 2009;62(3):656-64.
Braga, C.W., et al., Changes in lung volume and upper airway using MRI during application of nasal expiratory positive airway pressure in patients with sleep-disordered breathing. J Appl Physiol (1985), 2011. 111(5): p. 1400-9.
Capaldi, DPI, et al. Free-breathing Pulmonary MR Imaging to Quantify Regional Ventilation. Radiology. 2018;287 (2):693-704.
Capaldi, DPI, et al. Free-breathing Functional Pulmonary MRI: Response to Bronchodilator and Bronchoprovocation in Severe Asthma. Acad Radiol. 2017;24(10):1268-76. PubMed PMID: 28551402.
Castillo, R., et al. Ventilation from four-dimensional computed tomography: density versus Jacobian methods. Phys Med Biol. 2010;55(16):4661. PubMed PMID: 20671351.
Castillo, E., et al., Robust CT ventilation from the integral formulation of the Jacobian. Medical Physics, 2019. 0(0).
Castillo, E., Quadratic penalty method for intensity-based deformable image registration and 4DCT lung motion recovery. Medical Physics, 2019. 0(0).
Castillo, E., et al. Spatial correspondence of 4D CT ventilation and SPECT pulmonary perfusion defects in patients with malignant airway stenosis. Physics in Medicine and Biology. 2012;57(7):1855.
Castillo, E., et al. The numerical stability of transformation-based CT ventilation. Int J CARS. 2017;12(4):569-580.
Castillo, E., et al. Least median of squares filtering of locally optimal point matches for compressible flow image registration. Physics in Medicine and Biology. 2012;57(15):4827.
Castillo, E., et al. Computing global minimizers to a constrained B-spline image registration problem from optimal l1 perturbations to block match data. Medical Physics. 2014;41(4).
Castillo, E., et al. Compresible Image Registration for Thoracic Computed Tomography Images. Journal of Medical and Biological Engineering. 2009;29:222-233.
Castillo, R., et al. A framework for evaluation of deformable image registration spatial accuracy using large landmark point sets. Physics in Medicine and Biology. 2009;54(7):1849.
Castillo, E., et al. Four-dimensional deformable image registration using trajectory modeling. Physics in Medicine and Biology. 2010;55(1):305.
Christian, JA, et al. The incorporation of SPECT functional lung imaging into inverse radiotherapy planning for non-small cell lung cancer. Radiotherapy and oncology. 2005;77(3):271-277.
Cline, D., et al. Dart Throwing on Surfaces. Computer Graphics Forum. 2009;28(4):1217-1226.
Faught, AM, et al. Evaluating the Toxicity Reduction With Computed Tomographic Ventilation Functional Avoidance Radiation Therapy. International Journal of Radiation Oncology • Biology • Physics. 2017;99(2):325-333.
Grinnan, D.C. et al. Clinical review: respiratory mechanics in spontaneous and assisted ventilation. Crit Care, 2005. 9 (5): p. 472-84.
Guerrero, T., et al. Dynamic ventilation imaging from four-dimensional computed tomography. Physics in Medicine and Biology. 2006;51(4):777.
Guerrero, TM, et al. Quantification of regional ventilation from treatment planning CT. Int J Radiat Oncol Biol Phys. 2005;62(3):630-4. PubMed PMID: 15936537.
Hakim, TS., et al. Expiratory and inspiratory positive airway pressures in obstructive sleep apnea: how much pressure is necessary? A different point of view. J Lung Pulm Respir Res, 2015. 6(2): p. 134-138.
Higano, NS, et al. Hyperpolarized 3He Gas MRI in Infant Lungs: Investigating Airspace Size. A98 Seeing is believing: Using novel imaging techniques to understand the lung in health and disease: American Thoracic Society; 2017. p. A2663.
Hoffman, EA, et al. Pulmonary CT and MRI phenotypes that help explain chronic pulmonary obstruction disease pathophysiology and outcomes. J Magn Reson Imaging. 2015;43(3):544-57.
Huang, T-C, et al. IMRT treatment plans and functional planning with functional lung imaging from 4D-CT for thoracic cancer patients. Radiat Oncol. 2013;8(3).
Ireland, RH., et al. Feasibility of Image Registration and Intensity-Modulated Radiotherapy Planning With Hyperpolarized Helium-3 Magnetic Resonance Imaging for Non-Small-Cell Lung Cancer. International Journal of Radiation Oncology* Biology* Physics. 2007;68(1):273-281.
Jahani, N., et al., Assessment of regional ventilation and deformation using 4D-CT imaging for healthy human lungs during tidal breathing. J Appl Physiol (1985), 2015. 119(10): p. 1064-74.
Ding, Kai., et al. Comparison of Intensity- and Jacobian-Based Estimates of Lung Regional Ventilation. Paper presented at: Third International Workshop on Pulmonary Image Analysis, MICCAI 20102010.
Kern, AL, et al. Hyperpolarized gas MRI in pulmonology. Br J Radiol. 2018;91(1084):20170647.
Kipritidis, J., et al. Validating and improving CT ventilation imaging by correlating with ventilation 4D-PET/CT using 68Ga-labeled nanoparticles. Medical Physics. 2014;41(1):011910.
Kipritidis, J., et al. Measuring interfraction and intrafraction lung function changes during radiation therapy using four-dimensional cone beam CT ventilation imaging. Medical Physics. 2016;42(3):1255-1267.
Koehler, E., et al. On the Assessment of Monte Carlo Error in Simulation-Based Statistical Analyses. The American statistician. 2009;63(2):155-162.
Mai, C., et al., Thin-Section CT Features of Idiopathic Pulmonary Fibrosis Correlated with Micro-CT and Histologic Analysis. Radiology, 2017. 283(1): p. 252-263.
Mathew, L., et al. Hyperpolarized 3He Magnetic Resonance Imaging: Comparison with Four-dimensional X-ray Computed Tomography Imaging in Lung Cancer. Academic Radiology. 2012; 19(12):1546-1553.
Middleton, H., et al. MR Imaging with Hyperpolarized 3He Gas. Magn Reson Med. 1995;33(2):271-5. PubMed PMID: 7707920.
Mugler JP, et al. Hyperpolarized 129Xe MRI of the human lung. J Magn Reson Imaging. 2013;37(2):313-31.
Munawar, I., et al. Intensity modulated radiotherapy of non-small-cell lung cancer incorporating SPECT ventilation imaging. Medical Physics. 2010;37(4):1863-1872.

(56) References Cited

OTHER PUBLICATIONS

Pennati, F., et al. Assessment of Regional Lung Function with Multivolume 1H MR Imaging in Health and Obstructive Lung Disease: Comparison with 3He MR Imaging. Radiology. 2014;273(2):580-90.
Plantier, L., et al., Physiology of the lung in idiopathic pulmonary fibrosis. Eur Respir Rev, 2018. 27(147).
Sansores, R.H., et al., Correlation between pulmonary fibrosis and the lung pressure-volume curve. Lung, 1996. 174 (5): p. 315-23.
Simon, BA. Non-invasive imaging of regional lung function using x-ray computed tomography. J Clin Monit Comput. 2000;16(5-6):433-42. PubMed PMID: 12580227.
Guerrero, T., et al. Novel method to calculate pulmonary compliance images in rodents from computed tomography acquired at constant pressures. Physics in Medicine & Biology. 2006;51(5):1101.
Vinogradskiy, Y, et al. Regional Lung Function Profiles of Stage I and III Lung Cancer Patients: An Evaluation for Functional Avoidance Radiation Therapy. Int J Radiat Oncol Biol Phys. 2016;95(4):1273-80.
Vinogradskiy, Y., et al. Comparison of 4-Dimensional Computed Tomography Ventilation With Nuclear Medicine Ventilation-Perfusion Imaging: A Clinical Validation Study. International Journal of Radiation Oncology • Biology • Physics.(2014) 89(1):199-205.
Vinogradskiy, Y., et al. Use of 4-Dimensional Computed Tomography-Based Ventilation Imaging to Correlate Lung Dose and Function With Clinical Outcomes. International Journal of Radiation Oncology • Biology • Physics. (2013) 86 (2):366-371.
Waxweiler, T., et al. A complete 4DCT-ventilation functional avoidance virtual trial: Developing strategies for prospective clinical trials. Journal of Applied Clinical Medical Physics. 2017; 18(3):144-152.
Wild, JM., et al. Hyperpolarised Helium-3 (3He) MRI: Physical Methods for Imaging Human Lung Function. In: Kauczor H-U, Wielpütz MO, editors. MRI of the Lung. Cham: Springer International Publishing; 2018. p. 69-97. DOI: 10.1007/174_2017_45.
Woodruff, HC., et al. Quantifying the reproducibility of lung ventilation images between 4-Dimensional Cone Beam CT and 4-Dimensional CT. Medical Physics. 2017;44(5):1771-1781.
Yamamoto, T., et al. The first patient treatment of computed tomography ventilation functional image-guided radiotherapy for lung cancer. Radiother Oncol. 2016; 118(2):227-31. PubMed PMID: 26687903.
Yamamoto, T., Kabus S, Klinder T, et al. Four-dimensional computed tomography pulmonary ventilation images vary with deformable image registration algorithms and metrics. Medical Physics. 2011;38(3):1348-1358.
Yamamoto, T., et al. 4D CT lung ventilation images are affected by the 4D CT sorting method. Medical Physics. 2013;40(10):101907.
Yamamoto, T., et al. Reproducibility of Four-dimensional Computed Tomography-based Lung Ventilation Imaging. Academic Radiology. 2012; 19(12):1554-1565.
Yamamoto, T., et al. Impact of Four-Dimensional Computed Tomography Pulmonary Ventilation Imaging-Based Functional Avoidance for Lung Cancer Radiotherapy. International Journal of Radiation Oncology Biology Physics. 2011;79(1):279-288.
Yaremko, BP., et al. Reduction of normal lung irradiation in locally advanced non-small-cell lung cancer patients, using ventilation images for functional avoidance. International Journal of Radiation Oncology Biology Physics. 2007;68 (2):562-571.
Zha, W., et al. Regional Heterogeneity of Lobar Ventilation in Asthma Using Hyperpolarized Helium-3 MRI. Acad Radiol. 2018;25(2):169-78.
Reinhardt, J.M., et al.. Registration-based estimates of local lung tissue expansion compared to xenon CT measures of specific ventilation. Medical Image Analysis. 12(6):752-763.
Altose , M.D., Pulmonary Mechanics, in Fishman's Pulmonary Diseases and Disorders, A. Fishman, Editor 2008, Mc Graw Hill New York.
Oberkampf W, et al. Verification and Validation in Scientific Computing. Cambridge University Press; 2010.
Box GE, et al. Statistics for experimenters: design, innovation, and discovery. vol. 2: Wiley-Interscience New York; 2005.
Modersitzki, J., Numerical Methods for Image Registration. Numerical mathematics and scientific computation2004, New York: Oxford University Press.
Hammersley JM. Monte Carlo Methods. 1 ed: Springer Netherlands; 1964.
Hansen P, et al. Deblurring Images. doi: doi:10.1137/1.9780898718874: Society for Industrial and Applied Mathematics; 2006.
Wright S, et al. Numerical Optimization. vol. 2. New York: Springer; 1999.
Siva S, et al. High-resolution pulmonary ventilation and perfusion PET/CT allows for functionally adapted intensity modulated radiotherapy in lung cancer. Radiotherapy and Oncology. 115 (2015) pp. 157-162.

* cited by examiner

SYSTEMS AND METHODS FOR LUNG COMPLIANCE IMAGING

CROSS REFERENCE TO RELATED APPLICATIONS

This U.S. patent application is a continuation of, and claims priority to U.S. patent application Ser. No. 17/314,317, filed on May 7, 2021, which claims the benefit of U.S. Provisional Application 63/021,754, filed on May 8, 2020. The disclosures of these prior applications are considered part of the disclosure of this application and are hereby incorporated by reference in its entireties.

TECHNICAL FIELD

This disclosure relates to systems and methods for lung compliance imaging.

BACKGROUND

Lung compliance is the ability of the lung to expand with changes in pressure and is one of the earliest physiological measurements to be altered in patients with parenchymal lung disease. Routine monitoring of compliance could therefore potentially identify patients at risk for disease progression. However, in clinical practice, compliance measurements are prohibitively invasive for use as routine monitoring tools.

SUMMARY

One aspect of the disclosure provides a method for computing lung compliance imaging, the method comprising obtaining one or more images of lungs, determining a spatial transformation of each voxel within the lungs between the lungs at an inhale position and the lungs at an exhale position to provide displacement vector estimates for each voxel within the lungs, performing volume change inference operations to determine a volume change between the lungs at the inhale position and the lungs at the exhale position based on an inhale region of interest, an exhale region of interest, and the displacement vector estimates for each voxel within the lungs, and computing a lung compliance based on the volume change inference operations.

Implementations of the disclosure may include one or more of the following optional features. In some implementations, the lung compliance is calculated as $$LC(x) = \frac{vol(x) - J(x;\phi)\cdot vol(x)}{p_1 - p_2},$$

where $J(x; \phi)$ is the Jacobian, $\phi$ is the DIR solution, $p_1$ is a first pressure, and $p_2$ is a second pressure. The method may further comprise generating and displaying an LCI image for each lung voxel according to the lung compliance equation LC(x).

The images of the lungs of a patient may be obtained without the patient being mechanically ventilated. The images of the lungs may be obtained from one of four-dimensional computed tomography (4DCT), three-dimensional computed tomography (3DCT), or magnetic resonance imaging (MRI).

The volume change inference operations may include Jacobian operations. The images of the lungs may be obtained from breathhold inhale and exhale computed tomography pairs.

Another aspect of the disclosure provides a system comprising data processing hardware, and memory hardware in communication with the data processing hardware, the memory hardware storing instructions that when executed on the data processing hardware cause the data processing hardware to perform operations comprising obtaining one or more images of lungs, determining a spatial transformation of each voxel within the lungs between the lungs at an inhale position and the lungs at an exhale position to provide displacement vector estimates for each voxel within the lungs, performing volume change inference operations to determine a volume change between the lungs at the inhale position and the lungs at the exhale position based on an inhale region of interest, an exhale region of interest, and the displacement vector estimates for each voxel within the lungs, and computing a lung compliance based on the volume change inference operations.

This aspect may include one or more of the following optional features. In some implementations, the lung compliance is calculated as $$LC(x) = \frac{vol(x) - J(x;\phi)\cdot vol(x)}{p_1 - p_2},$$

where $J(x; \phi)$ is the Jacobian, $\phi$ is the DIR solution, $p_1$ is a first pressure, and $p_2$ is a second pressure. The operations may further comprise generating and displaying an LCI image for each lung voxel according to the lung compliance equation LC(x).

The images of the lungs of a patient are obtained without the patient being mechanically ventilated. The images of the lungs may be obtained from one of four-dimensional computed tomography (4DCT), three-dimensional computed tomography (3DCT), or magnetic resonance imaging (MRI).

The volume change inference operations may include Jacobian operations. The images of the lungs may be obtained from breathhold inhale and exhale computed tomography pairs.

Another aspect of the disclosure provides a computer program product encoded on a non-transitory computer readable storage medium comprising instructions that when executed by a data processing apparatus cause the data processing apparatus to perform operations comprising obtaining one or more images of lungs, determining a spatial transformation of each voxel within the lungs between the lungs at an inhale position and the lungs at an exhale position to provide displacement vector estimates for each voxel within the lungs, performing volume change inference operations to determine a volume change between the lungs at the inhale position and the lungs at the exhale position based on an inhale region of interest, an exhale region of interest, and the displacement vector estimates for each voxel within the lungs, and computing a lung compliance based on the volume change inference operations.

This aspect may include one or more of the following optional features. In some implementations, the lung compliance is calculated as $$LC(x) = \frac{vol(x) - J(x;\phi)\cdot vol(x)}{p_1 - p_2},$$

where $J(x; \phi)$ is the Jacobian, $\phi$ is the DIR solution, $p_1$ is a first pressure, and $p_2$ is a second pressure. The operations may further comprise generating and displaying an LCI image for each lung voxel according to the lung compliance equation LC(x).

The images of the lungs of a patient may be obtained without the patient being mechanically ventilated. The images of the lungs may be obtained from one of four-dimensional computed tomography (4DCT), three-dimensional computed tomography (3DCT), or magnetic resonance imaging (MRI). The images of the lungs may be obtained from breathhold inhale and exhale computed tomography pairs.

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

Figure 1:
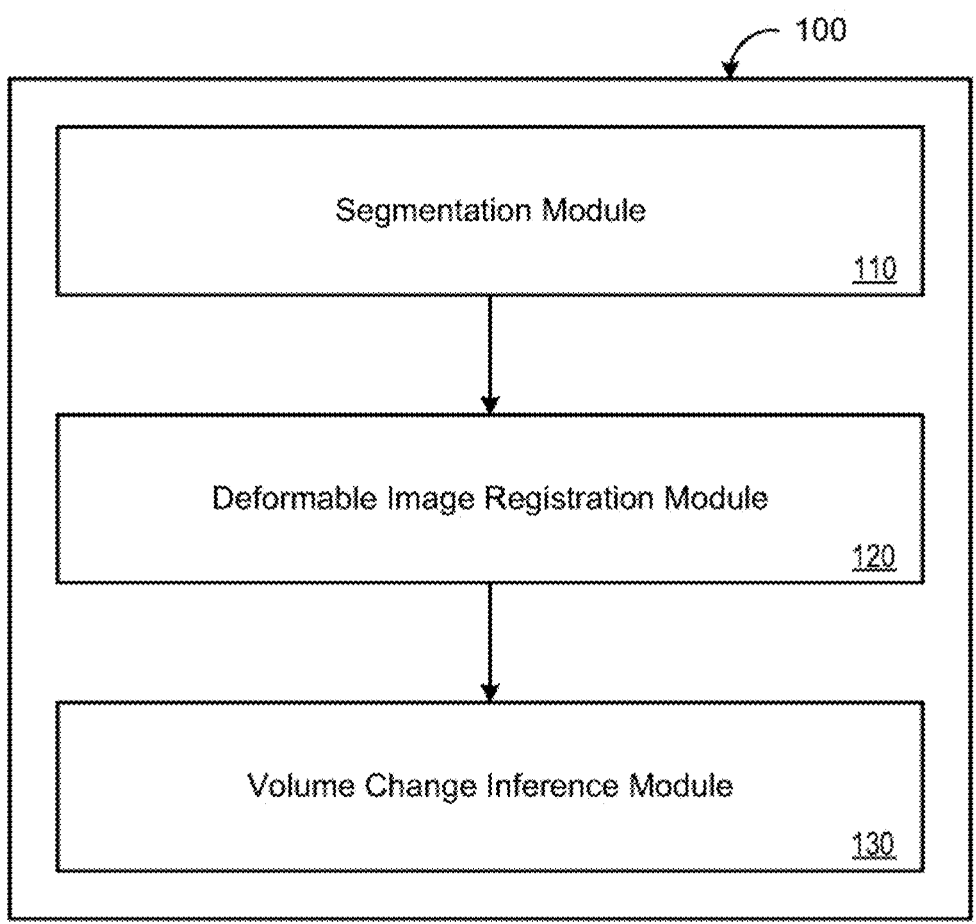
FIG. 1 is a schematic representation of an LCI system in accordance with principles of the present disclosure.

Example configurations will now be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

Lung compliance (LC) is a measure of the lung's ability to expand or contract with changes in pressure and is dependent upon the lung's elastic properties and surface tension. Lung compliance is one of the earliest physiological measurements to be altered in patients with parenchymal lung disease. For example, in patients with idiopathic pulmonary fibrosis (IPF), changes in regional lung function and stiffness may occur prior to the development of visually-appreciable radiographic changes. Thus, compliance monitoring could potentially aid in identifying IPF patients at risk for severe disease progression, thereby allowing for early treatments. However, in clinical practice, LC measurements require invasive monitoring, such as intra-pleural pressure measurement or esophageal manometry, and are not routinely calculated unless the patient is mechanically ventilated. Thus, a non-invasive methodology for computing compliance could potentially impact current IPF treatment practices.

Mathematically, lung compliance is calculated as the ratio of change in volume and change in pressure:

$$LC = \frac{\Delta V}{\Delta P} = \frac{V_1 - V_2}{P_1 - P_2} \tag{1}$$

where ΔV is the change in lung volume and ΔP is the change in trans-pulmonary pressure, which is defined as the relative pressure between the alveoli compared to the intra-pleural space. There are two types of LC: static and dynamic. Static LC is the change in volume for a specific pressure; usually measured when there is no flow within the airway at peak inspiration or end expiration. Dynamic LC is the compliance of the lung at any given time during tidal breathing. One of the many advantages of this disclosure is to introduce a non-invasive methodology for computing dynamic lung compliance imaging (LCI) from two non-contrast four-dimensional computed tomography (4DCT) scans acquired at different continuous positive airway pressures. The LCI system 100 described herein leverages recovering apparent lung voxel volume changes on free-breathing 4DCT scans as a surrogate for ventilation.

The physiological characteristics between changes in lung volume and pressure are non-linear. With inhalation, as the lung volume increases, the elastic elements within the lung approach maximum distension. Thus, normal compliance is higher during expiration than it is during inspiration. Several forces are acting within the lung parenchyma during free breathing that would affect the airway pressure and compliance. In a freely breathing patient, the measured pressure at the mouth would be affected by the resistance within the conducting airways and lung compliance (Opening Pressure=(Flow+resistance in airways)+alveolar volume changes/lung compliance). Magnetic resonance imaging (MRI) and positive pressure ventilation may demonstrate a consistent increase in the lung volume with positive pressure and reduced upper airway collapsibility.

Therefore, application of specific positive pressure via a non-invasive positive airway pressure ventilation (NIPPV) method would stabilize the pharyngeal pressure to the applied pressure, but the alveolar and pleural pressure continues to vary depending on patient effort. In a patient with fibrotic lung disease, the alveolar distension/volume change would be lower at each breath cycle on a lower pressure compared to a higher pressure.

4DCTs, which are also known as respiratory gated CTs, are volumetric CT images resolved into different phases of the breathing cycle. 4DCT is acquired while the patient is free-breathing and it may be used as a motion management tool in radiotherapy. During free breathing at two different pressures, other factors such as airway resistance and chest wall compliance may be similar and hence their effect may be minimal on a compliance measurement based on 4DCT scans.

CT-derived ventilation (CT-V) imaging applies mathematical modeling, image segmentation, and deformable image registration to 4DCT (or a pair of maximum inspiration-expiration CT scans) in order to quantify breathing-induced lung volume change as a surrogate for ventilation. While CT-V methods may be useful as a qualitative imaging marker for lung cancer radiotherapy planning, clinical applications for traditional CT-V algorithms may be limited due to a lack of robustness and reproducibility with respect to the image processing pipeline. The Integrated Jacobian Formulation (IJF) algorithm described herein may address numerical instability issues and may be robust to deformable image registration algorithm, and the resulting CT-V images may demonstrate a higher spatial correlation with 3D single photon emission CT-V than previous methods.

The IJF CT-V system may robustly recover the apparent volume change between inhale and exhale 4DCT phases. Considering that the Equation (1) compliance formulation requires computing lung volume at different pressures, the LCI system 100 may be based on applying the IJF algorithm to corresponding phases of two 4DCTs acquired under different pressure settings to recover dynamic compliance. Using 4DCT imaging acquired for patients with IPF and patients without IPF who had undergone lung nodule screening, it can be demonstrated that mean LCI values for IPF patients are significantly lower than those from the lung nodule cohort.

Referring to FIG. 1, the LCI system 100 includes a segmentation module 110, a deformable image registration (DIR) module 120, and a volume change inference module 130. The LCI system 100 may be configured to execute an LCI method 200. The LCI method 200 computes the Equation (1) compliance values for each voxel within a lung region of interest (ROI).

Figure 2:
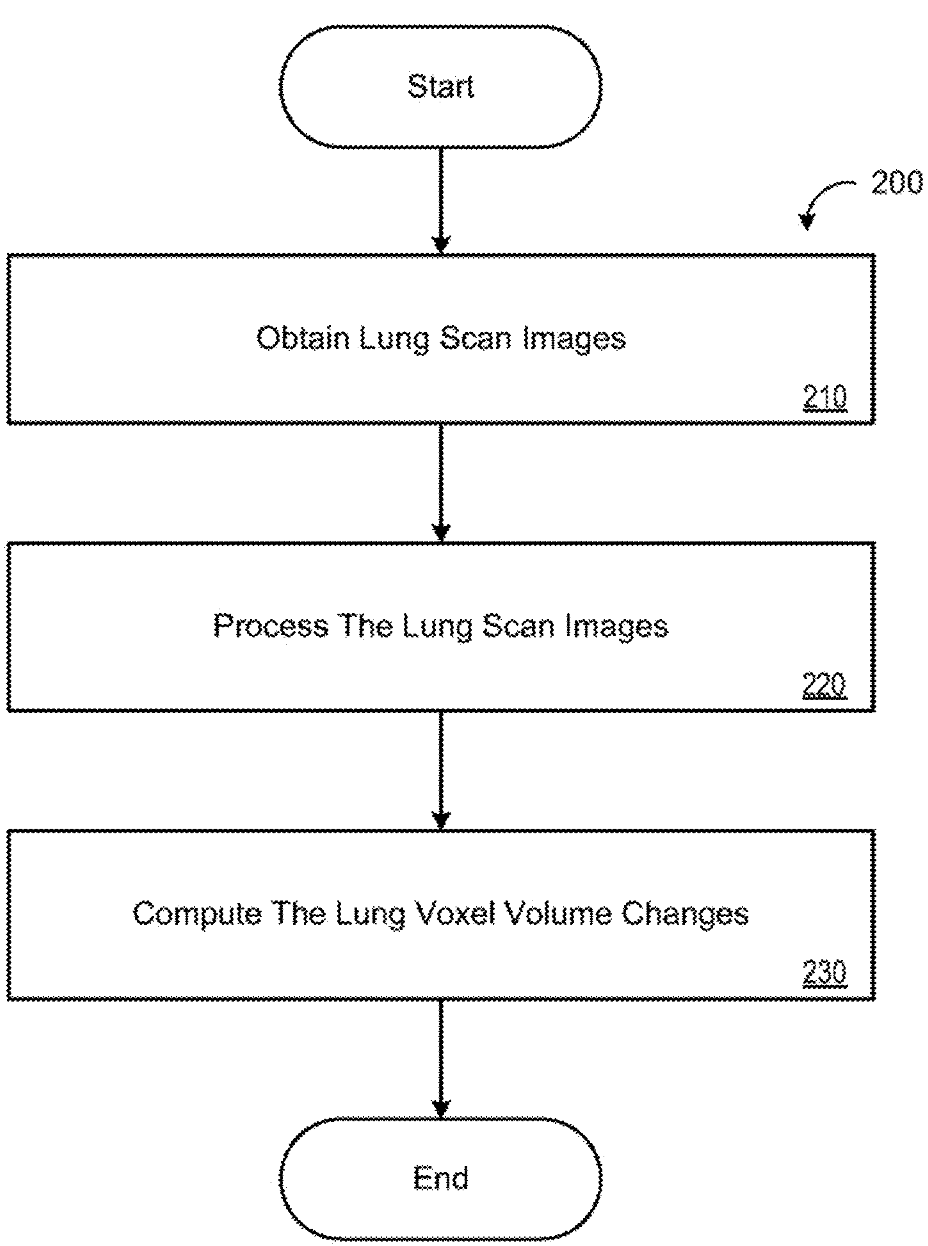
FIG. 2 is a flowchart of an LCI method executed by the LCI system of FIG. 1.

Referring to FIG. 2, the LCI method 200 may be based on three steps. The first step 210 is executed by the segmentation module 110, which may be configured to obtain or acquire two 4DCT scans, such as the 4DCT scan 310 shown in FIG. 3A. The first scan is acquired while the patient receives a continuous positive airway pressure (CPAP) of $p_1$, while the second scan is acquired under a CPAP of $p_2$. As one example, $p_1$=5 cm $H_2O$ and $p_2$=10 cm $H_2O$. 4DCT scans typically resolve the breathing cycle into 10 phases (images), denoted 0%, 10%, . . . , 90%, etc., where the 0% phase is the full inhale image and the 50% phase is the full exhale image. Corresponding phases from the two 4DCTs scans are selected to compute LCI. While the 0% phase is described herein and denoted as $$I_{p_1}^{0\%} \text{ and } I_{p_2}^{0\%},$$

respectively, it should be understood that the systems and methods described herein similarly apply to any phase pair, i.e., $$I_{p_1}^{k\%} \text{ and } I_{p_2}^{k\%},$$

where k=10, 20, . . . , 90, etc.

While the LCI system 100 and the LCI method 200 are described herein as obtaining images using computed tomography (3D or 4D), it should be understood that the LCI system 100 and the LCI method 200 may likewise obtain images using MRI or any other suitable imaging technique. Further, the imaging techniques described herein may be implemented without the patient being mechanically ventilated and without the use of contrast agents.

Figures 3A, 3B:
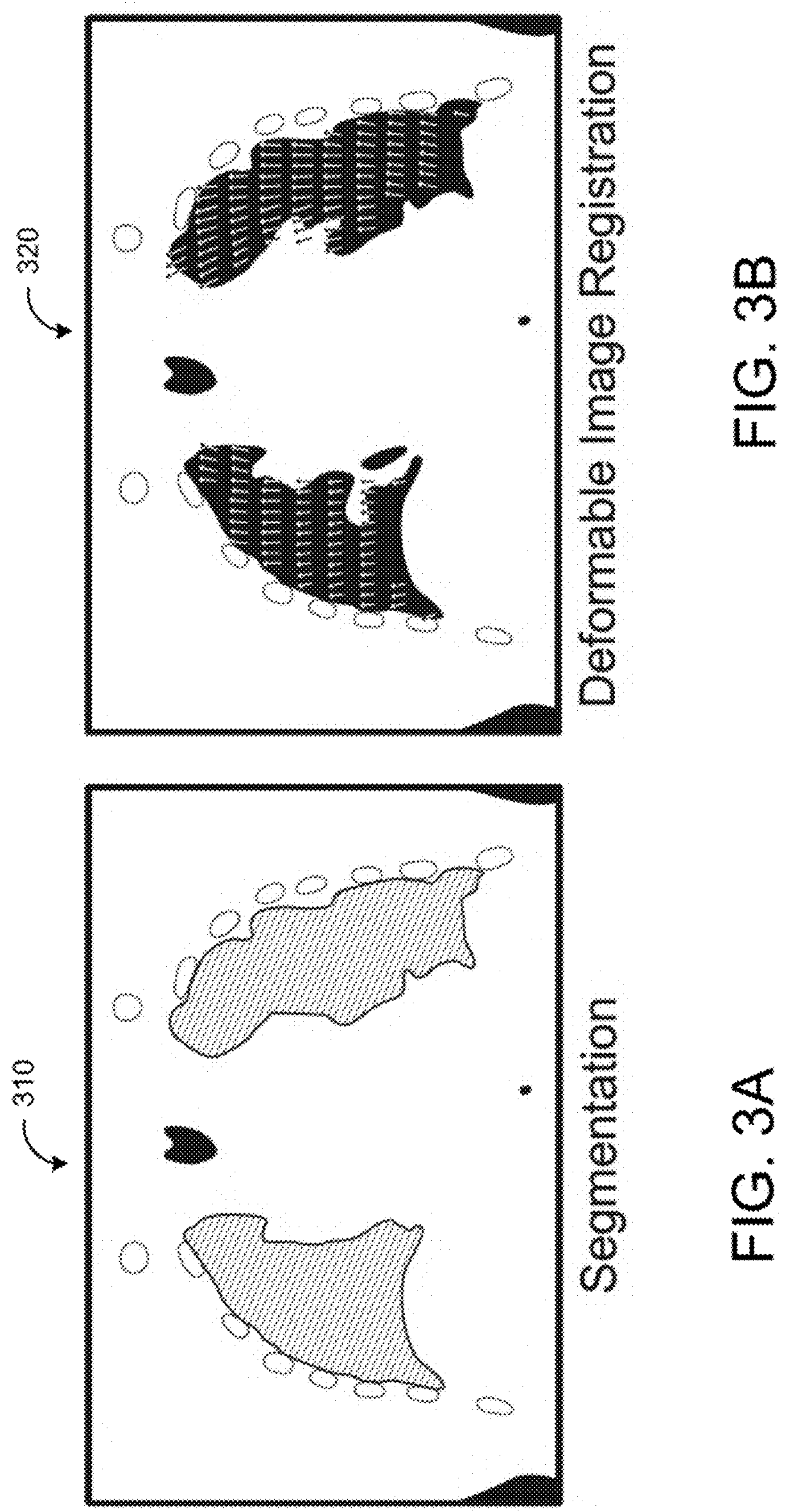
FIG. 3A is a 4DCT image of lungs with an image segmentation mask superimposed on the image.
FIG. 3B is a 4DCT image of lungs with a deformable image registration solution superimposed on the image.

The second step 220 of the LCI method 200 is executed by the DIR module 120, which may be configured to process the images of the 4DCT scans, such as the processed 4DCT scan 320 shown in FIG. 3B. The lung ROIs are segmented in the $$I_{p_1}^{0\%} \text{ and } I_{p_2}^{0\%},$$

images and then a deformable image registration algorithm is applied to recover the spatial deformation $\phi: \mathbb{R}^3 \rightarrow \mathbb{R}^3$ that maps the lung geometry in $$I_{p_1}^{0\%}$$

onto the one in $$I_{p_2}^{0\%}.$$

Accordingly, the LCI system 100 determines a spatial transformation of each voxel within the lungs between the lungs at an inhale position and the lungs at an exhale position to provide displacement vector estimates (represented by the arrows shown in FIG. 3B) for each voxel within the lungs.

The third step 230 of the LCI method 200 is executed by the volume change inference module 130, which may be configured to compute the lung voxel volume changes that are apparent between $$I_{p_1}^{0\%} \text{ and } I_{p_2}^{0\%}$$

using the IJF volume change estimation algorithm. The LCI method 200 uses the lung segmentations and the DIR solution $\phi$ to numerically recover the Jacobian, $J(x; \phi)$, which describes the volume scaling factor under $\phi$. Assuming $\phi$ is locally affine on a voxel volume x, $$vol(\phi(x)) = J(x; \phi) \cdot vol(x) \tag{2}$$

In other words, since $\phi$ represents the spatial mapping between the lung geometry at $p_1$ and the lung geometry at $p_2$, the Jacobian describes the change in volume induced by the change in pressure for each voxel in the lung ROI. Thus, for the voxel volume x in the $$I_{p_1}^{0\%}$$

image, the Equation (1) compliance can be computed as:

$$LC(x) = \frac{vol(x) - J(x; \phi) \cdot vol(x)}{p_1 - p_2} \tag{3}$$

The LCI system 100 computes a volumetric LCI image by evaluating Equation (3) for each voxel in the lung ROI. The resulting image provides a spatial map of the compliance for each lung voxel. Accordingly, the LCI system 100 determines a volume change between the lungs at the inhale position and the lungs at the exhale position based on the inhale ROI, the exhale ROI, and the displacement vector estimates for each voxel within the lungs.

The LCI system 100 may apply a series of image processing steps to the two phase images, $$I_{p_1}^{k\%} \text{ and } I_{p_2}^{k\%},$$

respectively, for the kth phase of two 4DCTs acquired under different continuous positive pressures. The LCI system 100 applies (i) image segmentation of the lung ROIs, (ii) deformable image registration to recover ϕ, and (iii) the IJF computation to recover J(x; ϕ). After computing these pre-processing steps, the LCI system 100 generates and displays an LCI image for each lung voxel according to Equation (3).

For image segmentation, the LCI system 100 employs an automated 3D densely connected convolutional network to generate an initial lung ROI. The LCI system 100 then refines the initial lung ROI to encapsulate the full lung volume. Such refinement may be completed automatically by the LCI system 100. Alternatively, such refinement may be manually done by, e.g., an imaging expert or any other suitable person.

The LCI system 100 may be configured to implement a modification of the Quadratic Penalty DIR (QPDIR) algorithm to compute to ϕ and $\phi^{-1}$ for the LCI method 200. QPDIR is designed around a gradient-free block coordinate descent strategy that iterates between block matching operations and linear least squares solves to maximize the image similarity. The LCI system 100 may include a penalty term in the QPDIR objective function to ensure lung ROI alignment. Given the lung ROIs and the DIR computed spatial transformation, the LCI system 100 may be configured to compute the Jacobian using a parameterized IJF method.

In order to account for variations in lung volume between different patients, the LCI system 100 may be configured to implement a normalized compliance metric:

$$C(x) = 1 - J(x;\phi) \tag{4}$$

Equation (4) is derived by dividing Equation (3) by the initial (undeformed) voxel volume at $p_1$ and ignoring the scalar change in pressure term ($p_1-p_2$), which is constant for all patients. Mean compliance is the mean of C(x) taken over all voxels in the $p_1$ lung volume, and compliance is computed for all 4DCT phases. The LCI system 100 may apply the Wilcoxon rank sum test to assess the significance of the difference between mean compliance values acquired for patients with IPF and mean compliance values acquired for the patients having suspicious lung nodules using the 0% phase. In some implementations, the images of the lung ventilation are generated and displayed including a color-gradient scale illustrating ventilation magnitude within the defined ROI of the lungs.

While the LCI system 100 and the LCI method 200 are described herein as implementing an IJF algorithm, it should be understood that the LCI system 100 and the LCI method 200 may likewise implement any suitable volume estimation model, including, but not limited to, CT-ventilation methods for calculating changes in air content, Hounsfield unit estimate of the Jacobian, and finite difference Jacobian methods.

Additionally, the LCI system 100 may compute static LCI in a variety of ways. As one example, static LCI may be measured using a three-dimensional computed tomography (3DCT) scan with breathhold at exhalation. For example, a first 3DCT image is obtained at full exhalation of the lungs at $p_1$, and a second 3DCT image is obtained at full exhalation at $p_2$. The LCI system 100 may then implement steps 220 and 230 as described above to determine LCI based on the volume estimation model set forth in the LCI method 200.

As another example for computing static LCI, the LCI system 100 may use two 3DCT scans: one scan of the lungs with breathhold at full inhalation at $p_1$ and another scan of the lungs with breathhold at full inhalation at $p_2$. The LCI system 100 may then implement steps 220 and 230 as described above to determine LCI based on the volume estimation model set forth in the LCI method 200. By obtaining pairs of images of the lungs with breathhold at full exhalation or breathhold at full inhalation, the LCI system 100 may produce pixel-level lung compliances.

Figure 4:
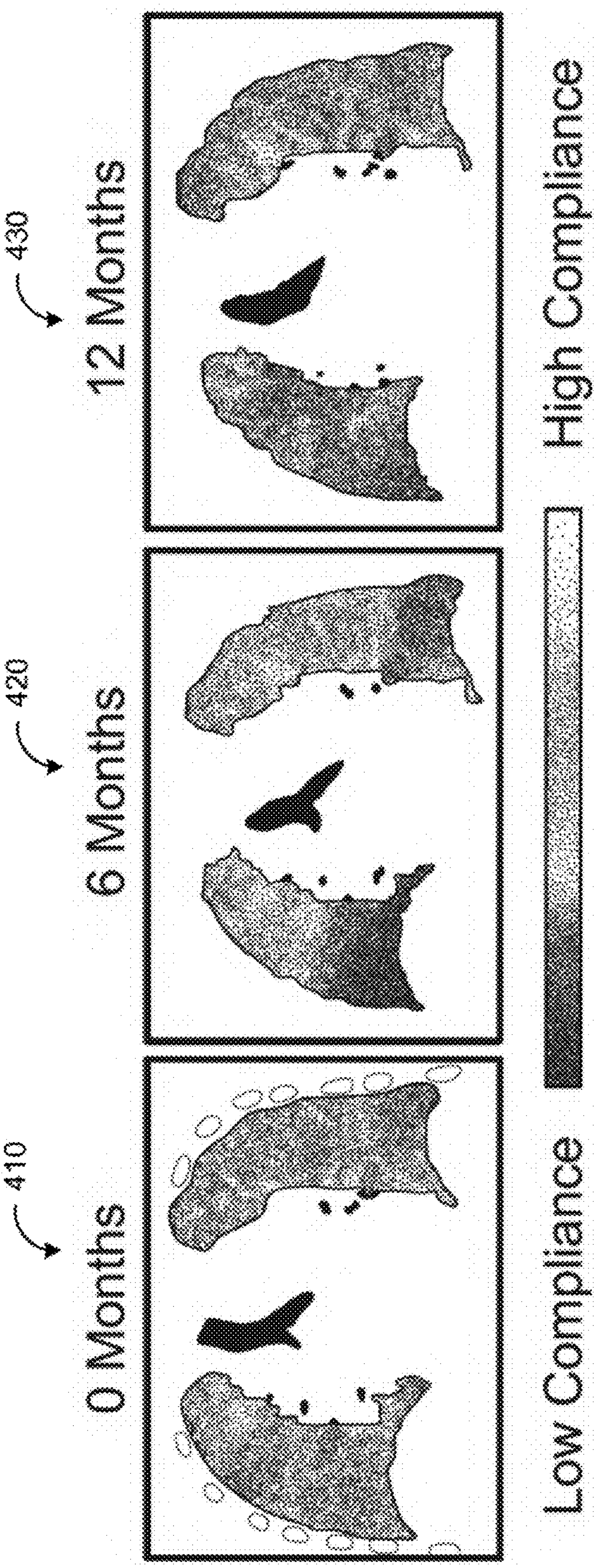
FIG. 4 is a series of 4DCT images of lungs of a patient with interstitial pulmonary fibrosis.

Referring to FIG. 4, a first LC image 410 taken at zero months, a second LC image 420 taken at 6 months, and a third LC image 430 taken at 12 months are generally shown for a patient with interstitial pulmonary fibrosis. As can be seen from the images, as the interstitial pulmonary fibrosis progresses, the compliance declines.

Figure 5:
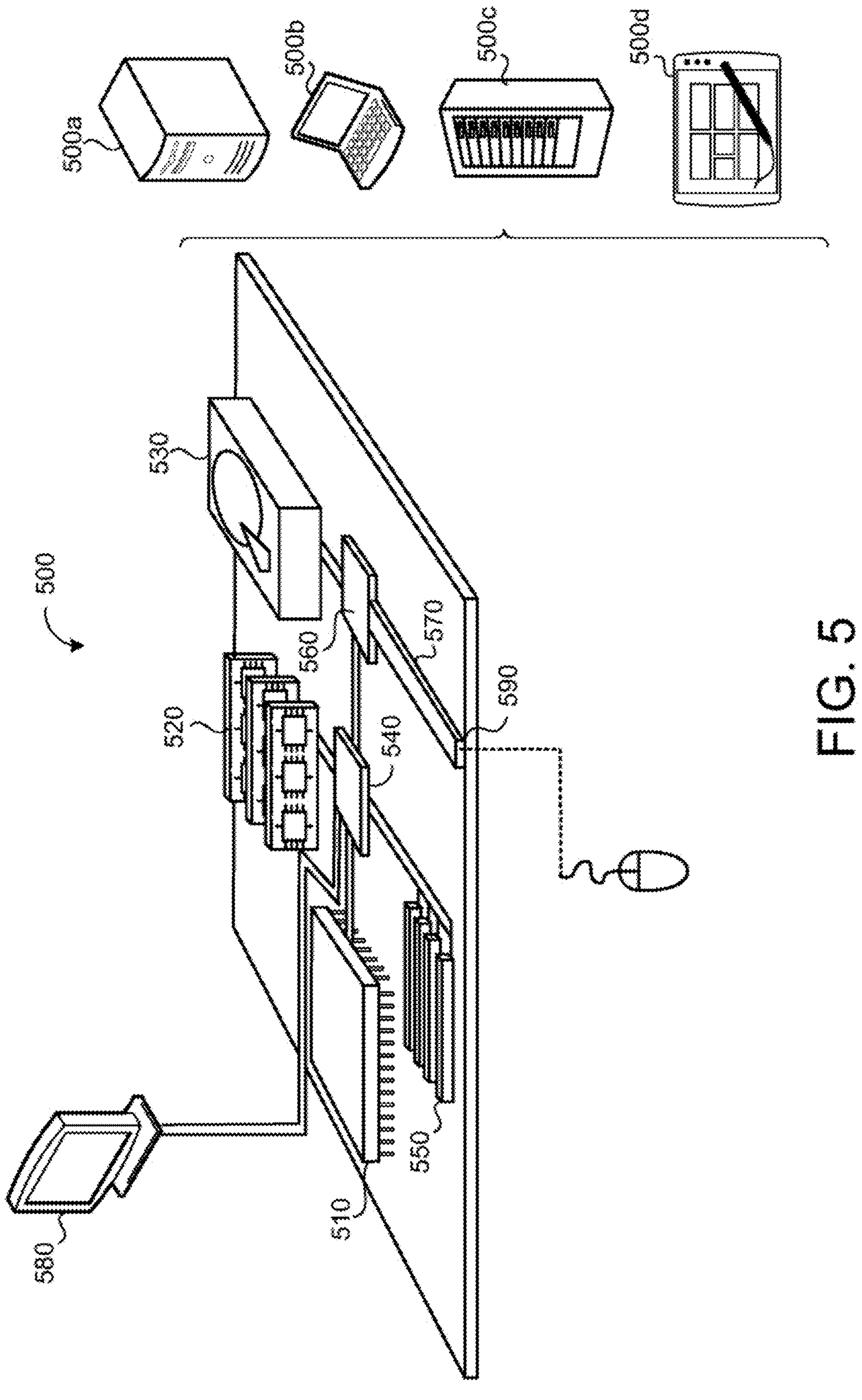
FIG. 5 is a schematic view of an example computing device that may be used to implement the systems and methods described herein.

FIG. 5 is schematic view of an example computing device 500 that may be used to implement the systems and methods described in this document. The computing device 500 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 500 includes a processor 510, memory 520, a storage device 530, a high-speed interface/controller 540 connecting to the memory 520 and high-speed expansion ports 550, and a low speed interface/controller 560 connecting to a low speed bus 570 and a storage device 530. Each of the components 510, 520, 530, 540, 550, and 560, are interconnected using various busses, and may be mounted on a common motherboard or in other manners as appropriate. The processor 510 can process instructions for execution within the computing device 500, including instructions stored in the memory 520 or on the storage device 530 to display graphical information for a graphical user interface (GUI) on an external input/output device, such as display 580 coupled to high speed interface 540. In other implementations, multiple processors and/or multiple buses may be used, as appropriate, along with multiple memories and types of memory. Also, multiple computing devices 500 may be connected, with each device providing portions of the necessary operations (e.g., as a server bank, a group of blade servers, or a multi-processor system).

The memory 520 stores information non-transitorily within the computing device 500. The memory 520 may be a computer-readable medium, a volatile memory unit(s), or non-volatile memory unit(s). The non-transitory memory 520 may be physical devices used to store programs (e.g., sequences of instructions) or data (e.g., program state information) on a temporary or permanent basis for use by the computing device 500. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 530 is capable of providing mass storage for the computing device 500. In some implementations, the storage device 530 is a computer-readable medium. In various different implementations, the storage device 530 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 520, the storage device 530, or memory on processor 510.

The high speed controller 540 manages bandwidth-intensive operations for the computing device 500, while the low speed controller 560 manages lower bandwidth-intensive operations. Such allocation of duties is exemplary only. In some implementations, the high-speed controller 540 is coupled to the memory 520, the display 580 (e.g., through a graphics processor or accelerator), and to the high-speed expansion ports 550, which may accept various expansion cards (not shown). In some implementations, the low-speed controller 560 is coupled to the storage device 530 and a low-speed expansion port 590. The low-speed expansion port 590, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 500*a* or multiple times in a group of such servers 500*a*, as a laptop computer 500*b*, as part of a rack server system 500*c*, or as a tablet computer 500*d*.

A software application (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

The non-transitory memory may be physical devices used to store programs (e.g., sequences of instructions) or data (e.g., program state information) on a temporary or permanent basis for use by a computing device. The non-transitory memory may be volatile and/or non-volatile addressable semiconductor memory. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A number of implementations have been described. Nevertheless, it will be understood that various modifications may be made without departing from the spirit and scope of the disclosure. Accordingly, other implementations are within the scope of the following claims.

What is claimed is:

1. A method for determining lung compliance, the method comprising:

based on a first image representative of a lung of a patient at a first continuous positive airway pressure (CPAP) and a second image representative of the lung at a second CPAP, determining a spatial transformation of a region of interest (ROI) within the lung;

based on the determined spatial transformation, determining a volume change for the ROI; and determining a lung compliance of the ROI based on the first CPAP, the second CPAP, and the determined volume change.

2. The method of claim 1, wherein the first image and the second image are representative of the lung during a selected phase of a respiratory cycle of the lung.

3. The method of claim 2, wherein the selected phase of the respiratory cycle comprises one selected from the group consisting of (i) a full inhale phase, and (ii) a full exhale phase.

4. The method of claim 1, wherein the first image and the second image are obtained from one selected from the group consisting of (i) four-dimensional computed tomography (4DCT), (ii) three-dimensional computed tomography (3DCT), and (iii) magnetic resonance imaging (MRI).

5. The method of claim 1, wherein the first image and the second image are obtained without the patient being mechanically ventilated.

6. The method of claim 1, wherein determining the spatial transformation of the ROI comprises applying a deformable image registration (DIR) algorithm to determine a displacement vector estimate between a voxel of the ROI in the first image and a corresponding voxel of the ROI in the second image.

7. The method of claim 6, wherein determining the volume change for the ROI comprises applying an Integrated Jacobian Formulation (IJF) to determine a volume scaling factor for the displacement vector estimate.

8. The method of claim 7, wherein determining the lung compliance (LC) of the voxel (x) of the ROI is calculated as $$LC(x) = \frac{vol(x) - (x; \phi) \cdot vol(x)}{p_1 - p_2},$$

where J(x; ϕ) is the volume scaling factor, ϕ is the displacement vector estimate, $p_1$ is the first CPAP, and $p_2$ is the second CPAP.

9. The method of claim 8, wherein determining the lung compliance of the ROI comprises determining the lung compliance of each voxel of a plurality of voxels of the ROI.

10. The method of claim 1, wherein the ROI comprises one selected from the group consisting of (i) a voxel, (ii) a lobe of the lung, and (iii) a full volume of the lung.

11. A system comprising:

memory hardware storing instructions that, when executed on data processing hardware in communication with the memory hardware, cause the data processing hardware to perform operations comprising:

based on a first image representative of a lung of a patient at a first continuous positive airway pressure (CPAP) and a second image representative of the lung at a second CPAP, determining a spatial transformation of a region of interest (ROI) within the lung;

based on the determined spatial transformation, determining a volume change for the ROI; and determining a lung compliance of the ROI based on the first CPAP, the second CPAP, and the determined volume change.

12. The system of claim 11, wherein the first image and the second image are representative of the lung during a selected phase of a respiratory cycle of the lung.

13. The system of claim 12, wherein the selected phase of the respiratory cycle comprises one selected from the group consisting of (i) a full inhale phase, and (ii) a full exhale phase.

14. The system of claim 11, wherein the first image and the second image are obtained from one selected from the group consisting of (i) four-dimensional computed tomography (4DCT), (ii) three-dimensional computed tomography (3DCT), and (iii) magnetic resonance imaging (MRI).

15. The system of claim 11, wherein the first image and the second image are obtained without the patient being mechanically ventilated.

16. The system of claim 11, wherein determining the spatial transformation of the ROI comprises applying a deformable image registration (DIR) algorithm to determine a displacement vector estimate between a voxel of the ROI in the first image and a corresponding voxel of the ROI in the second image.

17. The system of claim 16, wherein determining the volume change for the ROI comprises applying an Integrated Jacobian Formulation (IJF) to determine a volume scaling factor for the displacement vector estimate.

18. The system of claim 17, wherein determining the lung compliance (LC) of the voxel (x) of the ROI is calculated as $$LC(x) = \frac{vol(x) - J(x; \phi) \cdot vol(x)}{p_1 - p_2},$$

where J(x; ϕ) is the volume scaling factor, ϕ is the displacement vector estimate, $p_1$ is the first CPAP, and $p_2$ is the second CPAP.

19. The system of claim 18, wherein determining the lung compliance of the ROI comprises determining the lung compliance of each voxel of a plurality of voxels of the ROI.

20. The system of claim 11, wherein the ROI comprises one selected from the group consisting of (i) a voxel, (ii) a lobe of the lung, and (iii) a full volume of the lung.

* * * * *